United States Patent
Klosinski, Jr. et al.

(10) Patent No.: US 11,918,375 B2
(45) Date of Patent: Mar. 5, 2024

(54) WEARABLE ENVIRONMENTAL POLLUTION MONITOR COMPUTER APPARATUS, SYSTEMS, AND RELATED METHODS

(71) Applicant: BEIJING ZITIAO NETWORK TECHNOLOGY CO., LTD., Beijing (CN)

(72) Inventors: Richard Chester Klosinski, Jr., Sacramento, CA (US); Meghan Kathleen Murphy, Davis, CA (US); Matthew Allen Workman, Sacramento, CA (US); Jay William Sales, Sacramento, CA (US)

(73) Assignee: BEIJING ZITIAO NETWORK TECHNOLOGY CO., LTD. (CN)

( * ) Notice: Subject to any disclaimer, the term of this patent is extended or adjusted under 35 U.S.C. 154(b) by 0 days.

(21) Appl. No.: 16/449,759

(22) Filed: Jun. 24, 2019

(65) Prior Publication Data
US 2020/0397371 A1    Dec. 24, 2020

Related U.S. Application Data

(63) Continuation-in-part of application No. 14/846,401, filed on Sep. 4, 2015, now abandoned.
(Continued)

(51) Int. Cl.
*A61B 5/00* (2006.01)
*G01J 1/42* (2006.01)
(Continued)

(52) U.S. Cl.
CPC .......... *A61B 5/6803* (2013.01); *A61B 5/0077* (2013.01); *A61B 5/411* (2013.01);
(Continued)

(58) Field of Classification Search
CPC ...... G02B 2027/014; G02B 2027/0178; G02B 2027/0187; G02B 27/0093;
(Continued)

(56) References Cited

U.S. PATENT DOCUMENTS 3,505,879 A    4/1970    Vanderberg
3,548,663 A    12/1970   Radin
(Continued)

FOREIGN PATENT DOCUMENTS

EP    2778612    12/2017
GB    2396421     6/2004
(Continued)

OTHER PUBLICATIONS

Office Action, dated Jun. 8, 2018, from corresponding U.S. Appl. No. 14/610,501.
(Continued)

*Primary Examiner* — Yi-Shan Yang
*Assistant Examiner* — Alexei Bykhovski

(57) ABSTRACT

A system, according to various embodiments, includes eyewear (or any other suitable wearable device) that includes at least one environmental pollution monitoring sensor (e.g., at least one light pollution, air pollution, radioactive pollution, thermal pollution, and/or noise pollution sensor) that may be used to monitor the presence of environmental pollution adjacent a wearer of the eyewear. The system may further include one or more health monitoring sensors to determine the health effects of the environmental pollution on the wearer. In certain circumstances, the system may alert the user to potentially harmful environmental conditions, or convey preventative healthcare advice to the wearer.

18 Claims, 4 Drawing Sheets

Related U.S. Application Data

(60) Provisional application No. 62/135,612, filed on Mar. 19, 2015, provisional application No. 62/046,406, filed on Sep. 5, 2014.

(51) Int. Cl.
  *G01N 21/33* (2006.01)
  *G16H 40/67* (2018.01)

(52) U.S. Cl.
  CPC ............ *A61B 5/445* (2013.01); *A61B 5/7275* (2013.01); *G01J 1/429* (2013.01); *G01N 21/33* (2013.01); *G16H 40/67* (2018.01); *A61B 2560/0242* (2013.01)

(58) Field of Classification Search
  CPC ... G02B 27/0149; G02B 27/017; G06F 1/163; G06F 3/005; G06F 3/011; G06F 3/013; G06F 3/017; G06Q 30/02; A61B 2560/0242; A61B 5/0077; A61B 5/411; A61B 5/445; A61B 5/6803; A61B 5/7275; G01J 1/4204; G01J 1/429; G01J 2001/0257; G01N 21/33; G16H 40/67; G16H 50/30
  See application file for complete search history.

(56) References Cited

U.S. PATENT DOCUMENTS

| | | |
|---|---|---|
| 3,972,038 A | 7/1976 | Fletcher et al. |
| 4,100,401 A | 7/1978 | Tutt et al. |
| 4,186,609 A | 2/1980 | Baermann |
| 4,195,642 A | 4/1980 | Price et al. |
| 4,281,663 A | 8/1981 | Pringle |
| 4,407,295 A | 10/1983 | Steuer et al. |
| 4,434,801 A | 3/1984 | Jiminez et al. |
| 4,855,942 A | 8/1989 | Bianco |
| 4,878,749 A | 11/1989 | McGee |
| 4,919,530 A | 4/1990 | Hyman |
| 5,422,816 A | 6/1995 | Sprague et al. |
| 5,452,480 A | 9/1995 | Ryden |
| 5,497,143 A | 3/1996 | Matsuo et al. |
| 5,585,871 A | 12/1996 | Linden |
| 5,670,872 A | 9/1997 | Van De Walle et al. |
| 5,746,501 A | 5/1998 | Chien et al. |
| 5,891,042 A | 4/1999 | Sham et al. |
| 5,931,764 A | 8/1999 | Freeman et al. |
| 5,966,680 A | 10/1999 | Butnaru |
| 5,976,083 A | 11/1999 | Richardson et al. |
| 6,013,007 A | 1/2000 | Root et al. |
| 6,183,425 B1 | 2/2001 | Whalen et al. |
| 6,218,958 B1 | 4/2001 | Eichstaedt et al. |
| 6,241,684 B1 | 6/2001 | Amano et al. |
| 6,325,507 B1 | 12/2001 | Jannard et al. |
| 6,381,482 B1 | 4/2002 | Jayaraman et al. |
| 6,431,705 B1 | 8/2002 | Linden |
| 6,439,067 B1 | 8/2002 | Goldman et al. |
| 6,513,532 B2 | 2/2003 | Mault et al. |
| 6,532,298 B1 | 3/2003 | Cambier et al. |
| 6,736,759 B1 | 5/2004 | Stubbs et al. |
| 6,769,767 B2 | 8/2004 | Swab et al. |
| 6,783,501 B2 | 8/2004 | Takahashi et al. |
| 6,790,178 B1 | 9/2004 | Mault et al. |
| 6,812,845 B2 | 11/2004 | Yuzuki et al. |
| 7,181,345 B2 | 2/2007 | Rosenfeld et al. |
| 7,187,960 B2 | 3/2007 | Abreu |
| 7,192,136 B2 | 3/2007 | Howell et al. |
| 7,255,437 B2 | 8/2007 | Howell et al. |
| 7,376,238 B1 | 5/2008 | Rivas et al. |
| 7,380,936 B2 | 6/2008 | Howell et al. |
| 7,400,257 B2 | 7/2008 | Rivas |
| 7,401,918 B2 | 7/2008 | Howell et al. |
| 7,438,410 B1 | 10/2008 | Howell et al. |
| 7,454,002 B1 | 11/2008 | Gardner et al. |
| 7,457,434 B2 | 11/2008 | Azar |
| 7,481,531 B2 | 1/2009 | Howell et al. |
| 7,488,294 B2 | 2/2009 | Torch |
| 7,500,746 B1 | 3/2009 | Howell et al. |
| 7,500,747 B2 | 3/2009 | Howell et al. |
| 7,515,054 B2 | 4/2009 | Torch |
| 7,543,934 B2 | 6/2009 | Howell et al. |
| 7,581,833 B2 | 9/2009 | Howell et al. |
| 7,621,634 B2 | 11/2009 | Howell et al. |
| 7,630,524 B2 | 12/2009 | Lauper et al. |
| 7,634,379 B2 | 12/2009 | Noble |
| 7,640,135 B2 | 12/2009 | Vock et al. |
| 7,648,463 B1 | 1/2010 | Elhag et al. |
| 7,677,723 B2 | 3/2010 | Howell et al. |
| 7,771,046 B2 | 8/2010 | Howell et al. |
| 7,792,552 B2 | 9/2010 | Thomas et al. |
| 7,793,361 B2 | 9/2010 | Ishihara et al. |
| 7,857,772 B2 | 9/2010 | Bouvier et al. |
| 7,806,525 B2 | 10/2010 | Howell et al. |
| 7,922,321 B2 | 4/2011 | Howell et al. |
| 7,987,070 B2 | 7/2011 | Kahn et al. |
| 8,007,450 B2 | 8/2011 | Williams |
| 8,011,242 B2 | 9/2011 | O'Neill et al. |
| 8,081,082 B2 | 12/2011 | Malik et al. |
| 8,109,629 B2 | 2/2012 | Howell et al. |
| 8,157,730 B2 | 4/2012 | Leboeuf et al. |
| 8,188,868 B2 | 5/2012 | Case |
| 8,202,148 B2 | 6/2012 | Young |
| 8,290,558 B1 | 10/2012 | Lash et al. |
| 8,294,581 B2 | 10/2012 | Kamen |
| 8,303,311 B2 | 11/2012 | Forest |
| 8,337,013 B2 | 12/2012 | Howell et al. |
| 8,384,617 B2 | 2/2013 | Braun et al. |
| 8,430,507 B2 | 4/2013 | Howell et al. |
| 8,448,846 B2 | 5/2013 | Needham et al. |
| 8,449,471 B2 | 5/2013 | Tran |
| 8,465,151 B2 | 6/2013 | Howell et al. |
| 8,494,507 B1 | 7/2013 | Tedesco et al. |
| 8,500,271 B2 | 8/2013 | Howell et al. |
| 8,510,166 B2 | 8/2013 | Neven |
| 8,531,355 B2 | 9/2013 | Maltz |
| 8,540,583 B2 | 9/2013 | Leech |
| 8,568,313 B2 | 10/2013 | Sadhu |
| 8,594,971 B2 | 11/2013 | Keal et al. |
| 8,620,600 B2 | 12/2013 | Vock et al. |
| 8,630,633 B1 | 1/2014 | Tedesco et al. |
| 8,634,701 B2 | 1/2014 | Kang et al. |
| 8,647,270 B2 | 2/2014 | Leboeuf et al. |
| 8,690,750 B2 | 4/2014 | Krueger |
| 8,696,113 B2 | 4/2014 | Lewis |
| 8,733,928 B1 | 5/2014 | Lewis |
| 8,750,971 B2 | 6/2014 | Tran |
| 8,764,651 B2 | 7/2014 | Tran |
| 8,849,610 B2 | 9/2014 | Molettiere et al. |
| 8,892,401 B2 | 11/2014 | Yuen et al. |
| 8,905,542 B2 | 12/2014 | Howell et al. |
| 8,911,087 B2 | 12/2014 | Publicover et al. |
| 8,920,332 B2 | 12/2014 | Hong et al. |
| 8,931,896 B2 | 1/2015 | Blum et al. |
| 8,941,560 B2 | 1/2015 | Wong et al. |
| 8,944,590 B2 | 2/2015 | Blum et al. |
| 8,961,415 B2 | 2/2015 | Leboeuf et al. |
| 8,964,298 B2 | 2/2015 | Haddick et al. |
| 8,965,730 B2 | 2/2015 | Yuen |
| 8,979,295 B2 | 3/2015 | Waters |
| 9,001,427 B2 | 4/2015 | Jacobs et al. |
| 9,005,129 B2 | 4/2015 | Venkatraman et al. |
| 9,007,220 B2 | 4/2015 | Johns et al. |
| 9,028,405 B2 | 5/2015 | Tran |
| 9,031,812 B2 | 5/2015 | Roberts et al. |
| 9,033,493 B2 | 5/2015 | Howell et al. |
| 9,035,970 B2 | 5/2015 | Lamb et al. |
| 9,050,033 B2 | 6/2015 | Yoneyama et al. |
| 9,064,342 B2 | 6/2015 | Yuen et al. |
| 9,112,701 B2 | 8/2015 | Sano et al. |
| 9,113,793 B2 | 8/2015 | Terumoto et al. |
| 9,113,794 B2 | 8/2015 | Hong et al. |
| 9,113,795 B2 | 8/2015 | Hong et al. |
| 9,141,194 B1 | 9/2015 | Keyes et al. |

(56) References Cited

U.S. PATENT DOCUMENTS

| | | |
|---|---|---|
| 9,144,405 B2 | 9/2015 | Kim et al. |
| 9,149,212 B2 | 10/2015 | Mori |
| 9,153,074 B2 | 10/2015 | Zhou et al. |
| 9,215,290 B2 | 12/2015 | Yuen et al. |
| 9,229,227 B2 | 1/2016 | Border et al. |
| 9,235,064 B2 | 1/2016 | Lewis |
| 9,239,473 B2 | 1/2016 | Lewis |
| 9,241,635 B2 | 1/2016 | Yuen et al. |
| 9,244,293 B2 | 1/2016 | Lewis |
| 9,247,212 B2 | 1/2016 | Bose et al. |
| 9,254,100 B2 | 2/2016 | Beck et al. |
| 9,256,711 B2 | 2/2016 | Horseman |
| 9,267,800 B2 | 2/2016 | Doutaz et al. |
| 9,304,331 B2 | 4/2016 | Carrara |
| 9,341,526 B2 | 5/2016 | Bass et al. |
| 9,342,610 B2 | 5/2016 | Liu et al. |
| 9,480,877 B2 | 11/2016 | Chiang et al. |
| 9,520,638 B2 | 12/2016 | Baringer et al. |
| 9,529,197 B2 | 12/2016 | Olsson et al. |
| 9,566,033 B2 | 2/2017 | Bogdanovich et al. |
| 9,579,060 B1 | 2/2017 | Lisy et al. |
| 9,610,476 B1 | 4/2017 | Tran et al. |
| 9,726,904 B1 | 8/2017 | Lin |
| 9,763,592 B2 | 9/2017 | Le et al. |
| 9,782,128 B2 | 10/2017 | Lee et al. |
| 9,896,154 B2 | 2/2018 | Modolo |
| 9,977,259 B2 | 5/2018 | Archambeau et al. |
| 10,092,244 B2 | 10/2018 | Chuang et al. |
| 10,188,323 B2 | 1/2019 | Sales et al. |
| 10,310,296 B2 | 6/2019 | Howell et al. |
| 10,330,956 B2 | 6/2019 | Howell et al. |
| 10,349,887 B1 | 7/2019 | Tzvieli et al. |
| 10,398,328 B2 | 9/2019 | Kirenko et al. |
| 11,298,064 B1 * | 4/2022 | Lisy ............. A41D 1/002 |
| 2001/0031031 A1 | 10/2001 | Ogawa et al. |
| 2002/0151810 A1 | 10/2002 | Wong et al. |
| 2003/0195398 A1 | 10/2003 | Suzuki et al. |
| 2004/0039517 A1 | 2/2004 | Biesinger et al. |
| 2005/0033200 A1 | 2/2005 | Soehren et al. |
| 2005/0036103 A1 | 2/2005 | Bloch |
| 2005/0054942 A1 | 3/2005 | Melker et al. |
| 2006/0115130 A1 | 6/2006 | Kozlay |
| 2007/0052672 A1 | 3/2007 | Ritter et al. |
| 2007/0112287 A1 | 5/2007 | Fancourt et al. |
| 2007/0273611 A1 | 11/2007 | Torch |
| 2008/0137916 A1 | 6/2008 | Lauper et al. |
| 2009/0030350 A1 | 1/2009 | Yang et al. |
| 2009/0195747 A1 | 8/2009 | Insua |
| 2009/0227853 A1 | 9/2009 | Wijesiriwardana |
| 2009/0267805 A1 | 10/2009 | Jin et al. |
| 2010/0042430 A1 | 2/2010 | Bartfeld |
| 2010/0045928 A1 | 2/2010 | Levy |
| 2010/0110368 A1 | 5/2010 | Chaum |
| 2010/0117835 A1 * | 5/2010 | Nanikashvili ........ A61B 5/411 |
| | | 702/19 |
| 2010/0136508 A1 | 6/2010 | Zekhtser |
| 2010/0211425 A1 * | 8/2010 | Govindarajan ........................... |
| | | G06Q 10/063116 |
| | | 705/7.16 |
| 2010/0217099 A1 * | 8/2010 | LeBoeuf ............. G16H 20/30 |
| | | 600/301 |
| 2010/0271587 A1 | 10/2010 | Pavlopoulos |
| 2010/0280336 A1 | 11/2010 | Giftakis et al. |
| 2010/0308999 A1 | 12/2010 | Chornenky |
| 2010/0332571 A1 | 12/2010 | Healey et al. |
| 2011/0054359 A1 | 3/2011 | Sazonov et al. |
| 2011/0169932 A1 | 7/2011 | Mula et al. |
| 2011/0221656 A1 | 9/2011 | Haddick et al. |
| 2011/0224505 A1 | 9/2011 | Sadhu |
| 2012/0021806 A1 | 1/2012 | Maltz |
| 2012/0029367 A1 | 2/2012 | Hobeika |
| 2012/0127423 A1 | 5/2012 | Blum et al. |
| 2012/0133885 A1 | 5/2012 | Howell et al. |
| 2012/0135384 A1 | 5/2012 | Nakao |
| 2012/0142443 A1 | 6/2012 | Savarese et al. |
| 2012/0169990 A1 | 7/2012 | Burnstein |
| 2012/0191016 A1 | 7/2012 | Jastram |
| 2012/0203310 A1 | 8/2012 | Pugh et al. |
| 2012/0206485 A1 | 8/2012 | Osterhout et al. |
| 2012/0310442 A1 | 12/2012 | Doutaz et al. |
| 2013/0009907 A1 | 1/2013 | Rosenberg et al. |
| 2013/0024022 A1 | 1/2013 | Bowers |
| 2013/0024211 A1 | 1/2013 | Monteforte et al. |
| 2013/0041590 A1 | 2/2013 | Burich et al. |
| 2013/0050258 A1 | 2/2013 | Liu et al. |
| 2013/0096397 A1 | 4/2013 | Kiso et al. |
| 2013/0138413 A1 | 5/2013 | Finch et al. |
| 2013/0157232 A1 | 6/2013 | Ehrenkranz |
| 2013/0242262 A1 | 9/2013 | Lewis |
| 2013/0274587 A1 | 10/2013 | Coza et al. |
| 2013/0274904 A1 | 10/2013 | Coza et al. |
| 2013/0307670 A1 | 11/2013 | Ramaci |
| 2013/0329183 A1 | 12/2013 | Blum et al. |
| 2013/0345168 A1 | 12/2013 | Kim et al. |
| 2014/0028456 A1 | 1/2014 | Sadhu |
| 2014/0031703 A1 | 1/2014 | Rayner et al. |
| 2014/0063242 A1 | 3/2014 | Hanina et al. |
| 2014/0073081 A1 | 3/2014 | Wang |
| 2014/0078049 A1 | 3/2014 | Parshionikar |
| 2014/0085190 A1 | 3/2014 | Erinjippurath et al. |
| 2014/0135593 A1 | 5/2014 | Jayalth et al. |
| 2014/0142459 A1 | 5/2014 | Jayalth et al. |
| 2014/0159862 A1 | 6/2014 | Yang et al. |
| 2014/0204334 A1 | 7/2014 | Stoll |
| 2014/0207264 A1 | 7/2014 | Quy |
| 2014/0218281 A1 | 8/2014 | Amayeh et al. |
| 2014/0228649 A1 | 8/2014 | Rayner et al. |
| 2014/0229220 A1 | 8/2014 | Yuen et al. |
| 2014/0247145 A1 | 9/2014 | Proud |
| 2014/0266939 A1 * | 9/2014 | Baringer ............ A61B 5/02416 |
| | | 343/729 |
| 2014/0266988 A1 | 9/2014 | Fisher et al. |
| 2014/0276096 A1 | 9/2014 | Bonutti |
| 2014/0324459 A1 | 10/2014 | Barfield |
| 2014/0340221 A1 | 11/2014 | Yuen et al. |
| 2014/0346158 A1 | 11/2014 | Matthews |
| 2014/0375452 A1 | 12/2014 | Yuen et al. |
| 2014/0375470 A1 | 12/2014 | Malveaux |
| 2014/0378872 A1 | 12/2014 | Hong et al. |
| 2015/0057512 A1 | 2/2015 | Kapoor |
| 2015/0065889 A1 | 3/2015 | Gandelman et al. |
| 2015/0085245 A1 | 3/2015 | Howell et al. |
| 2015/0088464 A1 | 3/2015 | Yuen et al. |
| 2015/0148636 A1 | 5/2015 | Benaron |
| 2015/0173631 A1 | 6/2015 | Richards et al. |
| 2015/0179050 A1 | 6/2015 | Katingari et al. |
| 2015/0185506 A1 | 7/2015 | Lewis |
| 2015/0212329 A1 | 7/2015 | Sugihara et al. |
| 2015/0223805 A1 | 8/2015 | Whitman et al. |
| 2015/0244910 A1 | 8/2015 | Marston et al. |
| 2015/0281879 A1 | 10/2015 | Saadi |
| 2015/0287338 A1 | 10/2015 | Wells et al. |
| 2015/0332149 A1 | 11/2015 | Kolb et al. |
| 2015/0342482 A1 | 12/2015 | Carrara |
| 2015/0366518 A1 | 12/2015 | Sampson |
| 2016/0007849 A1 | 1/2016 | Krueger |
| 2016/0034042 A1 | 2/2016 | Joo |
| 2016/0041404 A1 | 2/2016 | Palermo et al. |
| 2016/0041613 A1 | 2/2016 | Klanner et al. |
| 2016/0066848 A1 | 3/2016 | Klosinski, Jr. et al. |
| 2016/0117937 A1 | 4/2016 | Penders et al. |
| 2016/0223577 A1 | 8/2016 | Klosinski, Jr. et al. |
| 2016/0314468 A1 | 10/2016 | Smith et al. |
| 2017/0071528 A1 | 3/2017 | Chen |
| 2017/0255029 A1 | 9/2017 | Klosinski, Jr. et al. |
| 2017/0265798 A1 | 9/2017 | Sales et al. |
| 2017/0323584 A1 | 11/2017 | Daniel et al. |
| 2018/0014737 A1 | 1/2018 | Paulussen et al. |
| 2018/0064399 A1 | 3/2018 | Buettgen et al. |
| 2018/0081201 A1 | 3/2018 | Lore et al. |
| 2018/0206735 A1 | 7/2018 | Holz et al. |
| 2018/0325422 A1 * | 11/2018 | Sokol ..................... A62B 7/10 |

(56) References Cited

U.S. PATENT DOCUMENTS

| | | | |
|---|---|---|---|
| 2019/0011703 A1* | 1/2019 | Robaina | G16H 20/40 |
| 2019/0216340 A1 | 7/2019 | Holz | |
| 2021/0082582 A1* | 3/2021 | Barrett | G16H 20/10 |

FOREIGN PATENT DOCUMENTS

| | | |
|---|---|---|
| WO | 2005015163 | 2/2005 |
| WO | 2005094667 | 10/2005 |
| WO | 2007088374 | 8/2007 |
| WO | 2008073806 | 6/2008 |
| WO | 2010006370 | 1/2010 |
| WO | 2010062479 | 6/2010 |
| WO | 2010062481 | 6/2010 |
| WO | 2011086466 | 7/2011 |
| WO | 2012041485 | 4/2012 |
| WO | 2013188343 | 12/2013 |
| WO | 2014021602 | 2/2014 |
| WO | 2014108481 | 7/2014 |
| WO | 2014144918 | 9/2014 |
| WO | 2014144940 | 9/2014 |
| WO | 2014170280 | 10/2014 |
| WO | 2014188244 | 11/2014 |
| WO | 2015015025 | 2/2015 |
| WO | 2015081299 | 6/2015 |
| WO | 2015095924 | 7/2015 |
| WO | 2015127143 | 8/2015 |
| WO | 2015127441 | 8/2015 |
| WO | 2016017997 | 2/2016 |
| WO | 2016029803 | 3/2016 |

OTHER PUBLICATIONS

Office Action, dated Mar. 21, 2019, from corresponding U.S. Appl. No. 16/259,646.
Office Action, dated Mar. 3, 2017, from corresponding U.S. Appl. No. 14/610,628.
Office Action, dated Mar. 8, 2016, from corresponding U.S. Appl. No. 14/610,628.
Office Action, dated Mar. 9, 2018, from corresponding U.S. Appl. No. 14/610,439.
Office Action, dated May 23, 2018, from corresponding U.S. Appl. No. 14/578,039.
Office Action, dated Nov. 30, 2017, from corresponding U.S. Appl. No. 14/550,406.
Office Action, dated Oct. 4, 2018, from corresponding U.S. Appl. No. 15/791,196.
Office Action, dated Sep. 11, 2018, from corresponding U.S. Appl. No. 15/060,333.
Office Action, dated Sep. 2, 2016, from corresponding U.S. Appl. No. 14/588,122.
Office Action, dated Sep. 26, 2017, from corresponding U.S. Appl. No. 14/846,401.
Office Action, dated Sep. 29, 2017, from corresponding U.S. Appl. No. 14/506,249.
Phend, Crystal, "Calorie Intake Rises as Sleep Time Drops," Medpage Today, Medpage Today, LLC, Mar. 15, 2012, Web Dec. 19, 2016, http://www.medpagetoday.com/cardiology/prevention/31663.
Restriction Requirement, dated Nov. 10, 2016, from corresponding U.S. Appl. No. 14/846,401.
Restriction Requirement, dated Oct. 4, 2017, from corresponding U.S. Appl. No. 14/610,439.
Restriction Requirement, dated Sep. 13, 2017, from corresponding U.S. Appl. No. 14/550,406.
Richard M. Satava, et al., "The Physiologic Cipher at Altitude: Telemedicine and Real-Time Monitoring of Climbers on Mount Everest", Telemedicine Journal and e-Health, vol. 6, No. 3, 2000, Mary Ann Liebert, Inc.
Shankland, Stephen, "Google's electronic eyewear get 'OK Glass' voice commands", Feb. 20, 2013, Cnet.com, https://www.cnet.com/news/googles-electronic-eyewear-gets-ok-glass-voice-commands/.
Ted Burnham, Wearable Air Quality Sensor: Tzoa, Jan. 5, 2015, Postscapes, http://www.postscapes.com/wearable-air-quality-sensor-tzoa/.
Tolentino, Mellisa, Udderly Clever Wearable Tech Solutions, http://siliconangle.com/blog/2014/03/25/udderly-clever-wearable-tech-solutions/, Mar. 25, 2014.
Torres, Juan Carlos, ODG R-7 Smart Glasses Carries Its Own Android Inside, http://androidcommunity.com/pdg-r-7-smart-glasses-carries-its-own-android-inside-20140919/, Sep. 19, 2014.
Written Opinion of the International Searching Authority, dated Dec. 18, 2015, from corresponding International Application No. PCT/US2015/048662.
Written Opinion of the International Searching Authority, dated Jan. 21, 2016, from corresponding International Application No. PCT/US2015/048612.
Written Opinion of the International Searching Authority, dated Jan. 21, 2016, from corresponding International Application No. PCT/US2015/048656.
Written Opinion of the International Searching Authority, dated Jun. 2, 2016, from corresponding International Application No. PCT/US2016/015705.
Final Office Action, dated Jul. 18, 2019, from corresponding U.S. Appl. No. 14/846,401.
Office Action, dated Jul. 26, 2019, from corresponding U.S. Appl. No. 16/259,646.
Notice of Allowance, dated Jul. 31, 2019, from corresponding U.S. Appl. No. 16/284,615.
Office Action, dated Aug. 6, 2019, from corresponding U.S. Appl. No. 16/429,480.
Office Action, dated Aug. 7, 2019, from corresponding U.S. Appl. No. 15/611,574.
Notice of Allowance, dated Sep. 11, 2019, from corresponding U.S. Appl. No. 16/259,646.
Office Action, dated Oct. 4, 2019, from corresponding U.S. Appl. No. 15/791,196.
Office Action, dated Nov. 15, 2019, from corresponding U.S. Appl. No. 16/527,544.
Notice of Allowance, dated Dec. 11, 2019, from corresponding U.S. Appl. No. 15/611,574.
Final Office Action, dated Apr. 29, 2019, from corresponding U.S. Appl. No. 15/791,196.
Final Office Action, dated Dec. 11, 2018, from corresponding U.S. Appl. No. 14/610,501.
Final Office Action, dated Dec. 15, 2016, from corresponding U.S. Appl. No. 14/506,249.
Final Office Action, dated Dec. 31, 2018, from corresponding U.S. Appl. No. 14/550,406.
Final Office Action, dated Jan. 14, 2019, from corresponding U.S. Appl. No. 14/578,039.
Final Office Action, dated Jan. 14, 2019, from corresponding U.S. Appl. No. 15/060,333.
Final Office Action, dated Jul. 10, 2017, from corresponding U.S. Appl. No. 14/846,401.
Final Office Action, dated Jun. 14, 2018, from corresponding U.S. Appl. No. 15/074,679.
Final Office Action, dated Jun. 30, 2017, from corresponding U.S. Appl. No. 14/610,589.
Final Office Action, dated Mar. 2, 2018, from corresponding U.S. Appl. No. 15/060,333.
Final Office Action, dated Mar. 29, 2017, from corresponding U.S. Appl. No. 14/562,454.
Final Office Action, dated Mar. 30, 2018, from corresponding U.S. Appl. No. 14/846,401.
Final Office Action, dated May 23, 2017, from corresponding U.S. Appl. No. 14/578,039.
Final Office Action, dated Nov. 16, 2017, from corresponding U.S. Appl. No. 14/610,628.
Final Office Action, dated Sep. 25, 2018, from corresponding U.S. Appl. No. 14/610,439.
Final Office Action, dated Sep. 26, 2016, from corresponding U.S. Appl. No. 14/610,628.

(56) References Cited

OTHER PUBLICATIONS

International Preliminary Report on Patentability, dated Mar. 16, 2017, from corresponding International Application No. PCT/US2015/048612.
International Preliminary Report on Patentability, dated Mar. 16, 2017, from corresponding International Application No. PCT/US2015/048656.
International Preliminary Report on Patentability, dated Mar. 16, 2017, from corresponding International Application No. PCT/US2015/048662.
International Search Report, dated Dec. 18, 2015, from corresponding International Application No. PCT/US2015/048662.
International Search Report, dated Jan. 21, 2016, from corresponding International Application No. PCT/US2015/048612.
International Search Report, dated Jan. 21, 2016, from corresponding International Application No. PCT/US2015/048656.
International Search Report, dated Jun. 2, 2016, from corresponding International Application No. PCT/US2016/015705.
Invitation to Pay Additional Search Fees, dated Apr. 1, 2016, from corresponding International Application Serial No. PCT/US2016/015705.
Invitation to Pay Additional Search Fees, dated Nov. 4, 2015, from corresponding International Application Serial No. PCT/US2015/048612.
Invitation to Pay Additional Search Fees, dated Nov. 4, 2015, from corresponding International Application Serial No. PCT/US2015/048656.
Jeannet, Pierre-Yves, et al., "Continuous monitoring and quantification of multiple parameters of daily physical activity in ambulatory Duchenne muscular, dystrophy patients", Official Journal of the European Paediatric Neurology Society, 2011.
Maria S. Redin, "Marathon Man", Article Jun. 15, 1998, MIT Media Laboratory.
Michael Franco, Tzoa wearable turns you into a walking air-quality sensor, Dec. 9, 2014, CNET, https://www.cnet.com/news/tzoa-wearable-turns-you-into-a-walking-air-quality-sensor/.
Notice of Allowance, dated Dec. 13, 2017, from corresponding U.S. Appl. No. 14/610,501.
Notice of Allowance, dated Feb. 28, 2017, from corresponding U.S. Appl. No. 14/588,122.
Notice of Allowance, dated Jan. 17, 2019, from corresponding U.S. Appl. No. 14/610,439.
Notice of Allowance, dated Jun. 21, 2017, from corresponding U.S. Appl. No. 14/562,454.
Notice of Allowance, dated Jun. 5, 2019, from corresponding U.S. Appl. No. 14/550,406.
Notice of Allowance, dated Oct. 11, 2018, from corresponding U.S. Appl. No. 15/074,679.
Notice of Allowance, dated Oct. 20, 2017, from corresponding U.S. Appl. No. 15/489,147.
Notice of Allowance, dated Sep. 13, 2018, from corresponding U.S. Appl. No. 15/594,898.
Office Action, dated Apr. 4, 2019, from corresponding U.S. Appl. No. 16/284,615.
Office Action, dated Aug. 19, 2016, from corresponding U.S. Appl. No. 14/578,039.
Office Action, dated Aug. 7, 2018, from corresponding U.S. Appl. No. 14/550,406.
Office Action, dated Dec. 29, 2016, from corresponding U.S. Appl. No. 14/610,589.
Office Action, dated Feb. 10, 2017, from corresponding U.S. Appl. No. 14/846,401.
Office Action, dated Feb. 11, 2019, from corresponding U.S. Appl. No. 14/846,401.
Office Action, dated Jan. 11, 2018, from corresponding U.S. Appl. No. 15/074,679.
Office Action, dated Jul. 1, 2016, from corresponding U.S. Appl. No. 14/562,454.
Office Action, dated Jul. 22, 2016, from corresponding U.S. Appl. No. 14/506,249.
Office Action, dated Jun. 11, 2019, from corresponding U.S. Appl. No. 14/610,501.
Office Action, dated Jun. 27, 2017, from corresponding U.S. Appl. No. 15/060,333.
Office Action, dated Jun. 27, 2019, from corresponding U.S. Appl. No. 15/060,333.
Office Action, dated Jun. 29, 2017, from corresponding U.S. Appl. No. 15/489,147.
Office Action, dated May 7, 2020, from corresponding U.S. Appl. No. 16/657,982.
Notice of Allowance, dated Mar. 24, 2020, from corresponding U.S. Appl. No. 16/527,544.
Notice of Allowance, dated Jan. 15, 2020, from corresponding U.S. Appl. No. 16/429,480.

\* cited by examiner

WEARABLE ENVIRONMENTAL POLLUTION MONITOR COMPUTER APPARATUS, SYSTEMS, AND RELATED METHODS

CROSS-REFERENCE TO RELATED APPLICATIONS

This application is a continuation-in-part of U.S. patent application Ser. No. 14/846,401, filed Sep. 4, 2015, entitled "WEARABLE ENVIRONMENTAL POLLUTION MONITOR COMPUTER APPARATUS, SYSTEMS, AND RELATED METHODS," which claimed priority to U.S. Provisional Patent Application Ser. No. 62/135,612, filed Mar. 19, 2015, entitled "WEARABLE ENVIRONMENTAL POLLUTION MONITOR COMPUTER APPARATUS, SYSTEMS, AND RELATED METHODS" and U.S. Provisional Patent Application Ser. No. 62/046,406, filed Sep. 5, 2014, entitled "WEARABLE HEALTH COMPUTER APPARATUS, SYSTEMS, AND RELATED METHODS", the disclosures of which are hereby incorporated by reference in their entirety.

BACKGROUND

Being able to detect the amount and type of environmental pollution directly affecting a particular person may be of great importance to that person—especially if they have a medical condition that is aggravated by environmental pollution. Accordingly, there is a need for effective systems and methods for monitoring and detecting localized environmental pollutants.

SUMMARY OF VARIOUS EMBODIMENTS

A computer-readable medium, according to various embodiments, comprises computer-executable instructions for: (1) receiving environmental pollution data from at least one environmental pollution sensor attached adjacent a wearable device; and (2) receiving health data from at least one health sensor attached adjacent the wearable device. The health data, in various embodiments, indicates at least one aspect of the health of a wearer of the wearable device. In various embodiments, the computer-readable medium further comprises computer-executable instructions for using the environmental pollution data and the health data to determine that a particular type and/or level of environmental pollution, as determined at least in part from the environmental pollution data, is associated with the at least one aspect of the wearer's health. In response to determining that the particular type and/or level of environmental pollution is associated with the at least one aspect of the wearer's health, the system may generate a message indicating the association between the particular type and/or level of environmental pollution and the at least one aspect of the wearer's health.

A computer system, according to various embodiments, comprises at least one computer processor and is configured for receiving environmental pollution data from a plurality of environmental sensors, each of the sensors being attached adjacent a respective particular wearable device (e.g., eyewear) that is being worn by a respective particular user while the user is located within a particular geographical zone. The system uses the pollution data from each of the plurality of environmental sensors to determine a respective level of a particular pollutant at a particular respective location within the particular geographical zone. The system may use the determined respective levels of the particular pollutant at particular respective locations within the particular geographical zone to determine an approximate aggregate level of the particular pollutant within the particular geographical zone.

A computer-implemented method, according to various embodiments, of monitoring environmental pollution adjacent a wearable device, comprises receiving, by at least one processor, environmental pollution data from at least one environmental pollution sensor attached adjacent a wearable device. The method further comprises receiving, by at least one processor, health data from at least one health sensor attached adjacent the wearable device. The health data indicates at least one aspect of the health of a wearer of the wearable device. The method further comprises using, by at least one processor, the environmental pollution data and the health data to determine that a particular type and/or level of environmental pollution, as determined at least in part from the environmental pollution data, is associated with the at least one aspect of the wearer's health. The method further comprises the step of using at least one processor to, in response to determining that the particular type and/or level of environmental pollution is associated with the at least one aspect of the wearer's health, generate a message indicating the association between the particular type and/or level of environmental pollution and the at least one aspect of the wearer's health.

BRIEF DESCRIPTION OF THE DRAWINGS

Various embodiments of systems and methods for assessing a level of environmental pollution are described below. In the course of this description, reference will be made to the accompanying drawings, which are not necessarily drawn to scale and wherein.

DETAILED DESCRIPTION OF SOME EMBODIMENTS

Figure 1:
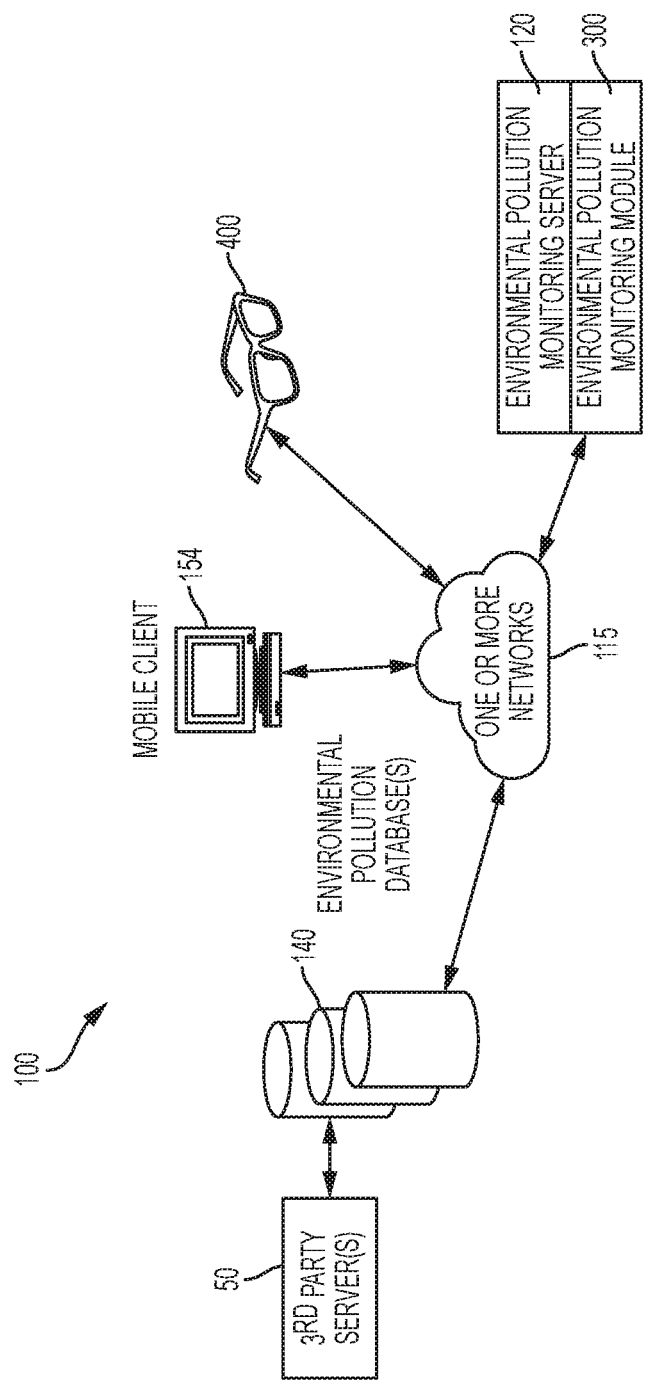
FIG. 1 is a block diagram of an Environmental Pollution Monitoring System in accordance with an embodiment of the present system.

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

A wearable environmental pollution monitoring system, in various embodiments, may, for example, be embodied in any suitable wearable device configured to monitor the physical condition of a wearer and/or the localized level of environmental pollution affecting the wearer. The system may, for example, be embodied as: (1) a pair of eyewear; (2) one or more contact lenses; (3) a wristwatch; (4) a suitable piece of clothing (e.g., a suitable shirt, pair of pants, undergarment, compression sleeve, etc.); (5) footwear; (6) a hat; (7) a helmet; (8) an orthopedic cast; or (9) any other suitable wearable item or other suitable item.

In various embodiments, the system comprises: (1) one or more pollution sensors, which are configured to determine an individual's exposure to one or more environmental pollutants; and/or (2) one or more health sensors to monitor the wearer's reaction to these pollutants. The one or more pollution and/or health sensors may be coupled to the wearable device in any suitable way. For instance, the one or more sensors may be embedded into the wearable device, coupled to the wearable device, and/or operatively coupled to the wearable device.

In various embodiments, the wearable environmental monitoring system may enable the system to determine a level of one or more environmental pollutants, (e.g., air pollutants, light pollutants, noise pollutants, radioactive pollutants, and/or thermal pollutants) using the environmental monitoring system's environmental pollution sensors when the environmental pollution monitoring system is worn by the wearer. The one or more pollution sensors may include, for example, one or more air sampling devices, one or more light pollutant samplers (e.g., one or more devices for measuring light pollutants such as ultraviolet light and blue light), one or more noise pollutant samplers, one or more radioactive pollutant monitors, one or more thermal pollutant samplers, and/or one or more ultraviolet light measurement devices.

In various embodiments, the wearable environmental monitoring system may enable the system to determine the reaction of the wearer to one or more environmental pollutants by using the environmental monitoring system's one or more health sensors. In various embodiments, the one or more health sensors measure a physical reaction of the wearer to various environmental pollutants by monitoring certain characteristics of the wearer including, for example, changes in: pupil size, skin coloration, heart rate, perspiration level, composition of the wearer's perspiration, respiration rate, movement, brainwave activity, and/or any other suitable characteristics. The one or more health sensors may include, for example, one or more heart rate monitors, one or more electrocardiograms (EKGs), one or more electroencephalograms (EEGs), one or more thermometers, one or more transdermal sensors, one or more blood pressure sensors, one or more pulse oximeters, one or more respiration rate monitors, one or more front-facing cameras, one or more eye-facing cameras, one or more communication sensors, or any other suitable one or more sensors.

In various embodiments, the system is configured to associate the wearer's physical reaction with one or more environmental pollutants based, at least in part, on the received health data and environmental pollution signals. For example, if the system senses that the wearer has an otherwise unexplained increase in heart rate or respiratory rate, and the system senses the presence of a particular environmental pollutant, the system may determine that the wearer is having an adverse reaction to the environmental pollutant.

After determining that a wearer is having a possible adverse reaction to a particular pollutant, the system may notify the wearer or a third party (e.g., the wearer's physician) of the possible adverse reaction. In particular embodiments, the system may notify the wearer via the wearable device or through a notification sent to a mobile computing device or other computing device associated with the wearer or other individual. The system may also provide the wearer with one or more suggestions on how to address the wearer's current physical state. For instance, if the wearer is having an adverse reaction to a particular pollutant, the system may suggest that the wearer utilize one or more medications, or take other preventative or ameliorating measures to reduce the effects of the adverse reaction. In particular embodiments, the system may also, or alternatively, store the determined environmental pollutant level (e.g., pollutant concentration or exposure level), data regarding the user's physical state, and any related information in computer memory for later analysis.

In various embodiments, while the system is using one or more environmental pollution sensors (e.g., eyewear based sensors) to assess the level of environmental pollutants, the system may also (e.g., at least substantially simultaneously) capture one or more images of a wearer and/or one or more visible pollutants (e.g., smog or UV light radiation) located in close proximity to the wearer (e.g., using a camera, such as a forward or rear facing camera associated with eyewear worn by the wearer). In various embodiments, the system may then analyze the image to further assess the user's exposure and reaction to a particular pollutant (e.g., intense sunlight). The system may then provide one or more suggestions to the wearer as to how to avoid any adverse reaction to the environmental pollutants prior to (or after) the physical manifestation of any symptoms.

Exemplary Technical Platforms

As will be appreciated by one skilled in the relevant field, the present systems and methods may be, for example, embodied as a computer system, a method, or a computer program product. Accordingly, various embodiments may be entirely hardware or a combination of hardware and software. Furthermore, particular embodiments may take the form of a computer program product stored on a computer-readable storage medium having computer-readable instructions (e.g., software) embodied in the storage medium. Various embodiments may also take the form of Internet-implemented computer software. Any suitable computer-readable storage medium may be utilized including, for example, hard disks, compact disks, DVDs, optical storage devices, and/or magnetic storage devices.

Various embodiments are described below with reference to block diagram and flowchart illustrations of methods, apparatuses, (e.g., systems), and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, a special purpose computer, or other programmable data processing apparatus that can direct a computer or other programmable data processing apparatus to function in a particular manner such that the instructions stored in the computer-readable memory produce an article of manufacture that is configured for implementing the functions specified in the flowchart block or blocks.

The computer instructions may execute entirely on the user's computer, partly on the user's computer, as a stand-alone software package, partly on a user's computer and partly on a remote computer, or entirely on the remote computer or server. In the latter scenario, the remote computer may be connected to the user's computer through any suitable type of network, including but not limited to: a local area network (LAN); a wide area network (WAN), such as the Internet; and/or a cellular network.

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer-implemented process (e.g., method) such that the instructions that execute on the computer or other programmable apparatus provide steps for implementing the functions specified in the flowchart block or blocks.

Example System Architecture

FIG. 1 is a block diagram of an Environmental Pollution Monitoring System 100 according to particular embodiments. As may be understood from this figure, the Environmental Pollution Monitoring System 100 includes One or More Networks 115, One or More Third Party Servers 50, an Environmental Pollution Monitoring Server 120 that may, for example, be adapted to execute an Environmental Pollution Monitoring Module 300, one or more Databases 140 (e.g., one or more Environmental Pollution Databases), One or More Remote Computing Devices 154 (e.g., a smart phone, a tablet computer, a wearable computing device, a laptop computer, a desktop computer, etc.), and One or More Environmental Pollution Monitoring Devices 400, which may, for example, be embodied as eyewear, headwear, clothing, a watch, a hat, a helmet, a cast, an adhesive bandage, a piece of jewelry (e.g., a ring, earring, necklace, bracelet, brooch, etc.), or any other suitable wearable device or other device (e.g., other computing device). In particular embodiments, the one or more computer networks 115 facilitate communication between the One or More Third Party Servers 50, the Environmental Pollution Monitoring Server 120, the one or more Databases 140, the One or More Remote Computing Devices 154, and the one or more Environmental Pollution Monitoring Devices 400.

The one or more networks 115 may include any of a variety of types of wired or wireless computer networks such as the Internet (or other WAN), a private intranet, a mesh network, a public switch telephone network (PSTN), and/or any other type of network (e.g., a network that uses Bluetooth or near field communications to facilitate communication between computing devices). The communication link between the One or More Remote Computing Devices 154 and the Environmental Pollution Monitoring Server 120 may be, for example, implemented via a Local Area Network (LAN) or via the Internet (or other WAN).

Figure 2:
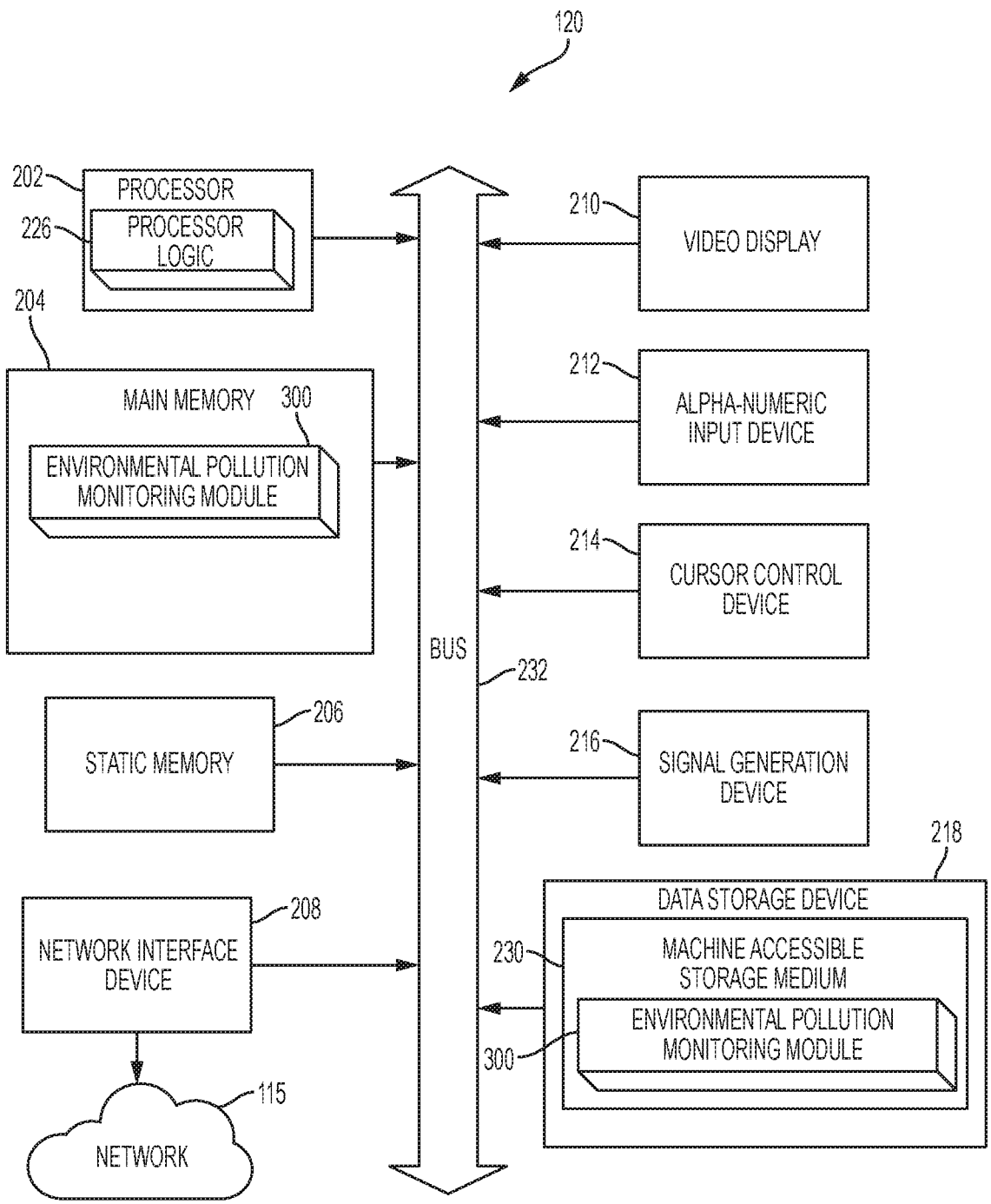
FIG. 2 is a block diagram of the Environmental Monitoring Pollution Server of FIG. 1.

FIG. 2 illustrates a diagrammatic representation of an exemplary architecture of an Environmental Pollution Monitoring Server 120 that may be used within various embodiments of the Environmental Pollution Monitoring System 100. It should be understood that the computer architecture shown in FIG. 2 may also represent the computer architecture for any one of the One or More Remote Computing Devices 154, one or more Third Party Servers 50, and/or the One or More Health Monitoring Devices 400 shown in FIG. 1. In particular embodiments, the Environmental Pollution Monitoring Server 120 may be suitable for use as a computer within the context of the Environmental Pollution Monitoring System 100 that is configured to determine the environmental pollution near a wearer by detecting one or more characteristics of pollution using one or more signals received from one or more sensors coupled to the one or more Health Monitoring Devices 400. In other particular embodiments, the Environmental Pollution Monitoring Device 400 may include an on-board computer processor that is adapted to execute an Environmental Pollution Monitoring Module 300 to determine the environmental pollution near the wearer.

In particular embodiments, the Environmental Pollution Monitoring Server 120 may be connected (e.g., networked) to other computing devices in a LAN, an intranet, an extranet, and/or the Internet as shown in FIG. 1. As noted above, the Environmental Pollution Monitoring Server 120 may operate in the capacity of a server or a client computing device in a client-server network environment, or as a peer computing device in a peer-to-peer (or distributed) network environment. The Environmental Pollution Monitoring Server 120 may be a desktop personal computing device (PC), a tablet PC, a set-top box (STB), a Personal Digital Assistant (PDA), a smartphone, a web appliance, a network router, a switch or bridge, or any other computing device capable of executing a set of instructions (sequential or otherwise) that specify actions to be taken by that computing device. Further, while only a single computing device is illustrated, the term "computing device" shall also be interpreted to include any collection of computing devices that individually or jointly execute a set (or multiple sets) of instructions to perform any one or more of the methodologies discussed herein, or other suitable methodologies.

As shown in FIG. 2, an exemplary Environmental Pollution Monitoring Server 120 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose or specific processing devices such as a microprocessor, a central processing unit (CPU), or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gate array (FPGA), a digital signal processor (DSP), network processor, or the like. The processing device 202 may be configured to execute processing logic 226 for performing various operations and steps discussed herein.

The Environmental Pollution Monitoring Server 120 may further include a network interface device 208. The Environmental Pollution Monitoring Server 120 may also include a video display unit 210 (e.g., a liquid crystal display (LCD) or a cathode ray tube (CRT)), an alpha-numeric input device 212 (e.g., a keyboard), a cursor control device 214 (e.g., a mouse), a signal generation device 216 (e.g., a speaker), and a data storage device 218.

The data storage device 218 may include a non-transitory computing device-accessible storage medium 230 (also known as a non-transitory computing device-readable storage medium, a non-transitory computing device-readable medium, or a non-transitory computer-readable medium) on which is stored one or more sets of instructions (e.g., the Environmental Pollution Monitoring Module 300) embodying any one or more of the methodologies or functions described herein. The one or more sets of instructions may also reside, completely or at least partially, within the main memory 204 and/or within the processing device 202 during execution thereof by the Environmental Pollution Monitoring Server 120—the main memory 204 and the processing device 202 also constituting computing device-accessible storage media. The one or more sets of instructions may further be transmitted or received over a network 115 via a network interface device 208.

While the computing device-accessible storage medium 230 is shown in an exemplary embodiment to be a single medium, the term "computing device-accessible storage medium" should be understood to include a single medium or multiple media (e.g., a centralized or distributed database, and/or associated caches and servers) that store the one or more sets of instructions. The term "computing device-accessible storage medium" should also be understood to include any medium that is capable of storing, encoding, or carrying a set of instructions for execution by the computing device and that causes the computing device to include any one or more of the methodologies of the present invention. The terms "computing device-accessible storage medium" and like terms should accordingly be understood to include, but not be limited to, solid-state memories, optical and magnetic media, etc.

Exemplary Environmental Pollution Monitoring Device

Figure 4:
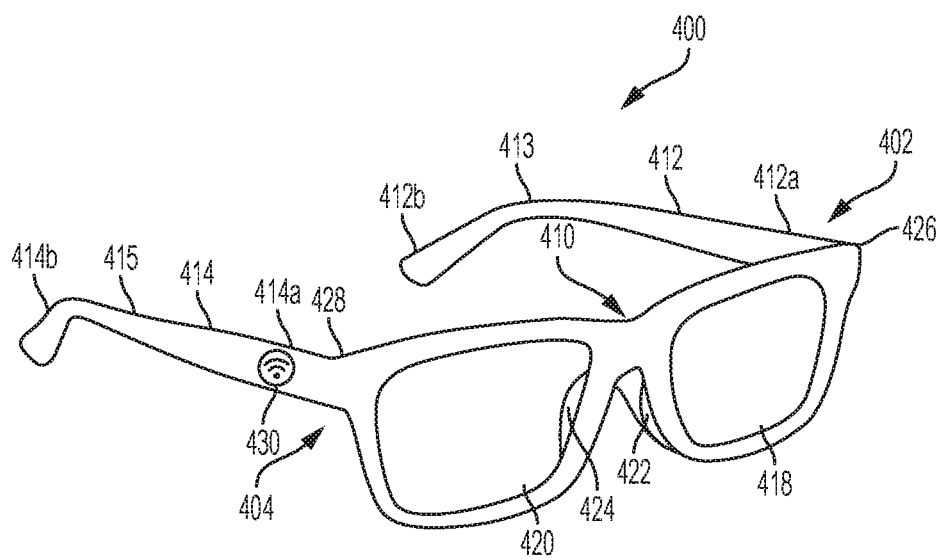
FIG. 4 is an exemplary wearable health monitoring device for use in the Environmental Pollution Monitoring System of FIG. 1.

As shown in FIG. 1, the Environmental Pollution Monitoring System 100, in various embodiments, comprises One or More Environmental Pollution Monitoring Devices 400. A particular embodiment of an environmental pollution monitoring device is shown in FIG. 4 as eyewear 400. As shown in this figure, eyewear 400, according to various embodiments, includes: (1) an eyewear frame 410; (2) a first temple 412; and (3) a second temple 414. These various components are discussed in more detail below.

Eyewear Frame

Referring still to FIG. 4, eyewear 400, in various embodiments, includes any suitable eyewear frame 410 that is configured to support one or more lenses 418, 420. In the embodiment shown in this figure, the eyewear frame 410 defines a first end 402 and a second end 404. The eyewear frame 410 may be made of any suitable material such as metal, ceramic, one or more polymers or any combination thereof. In particular embodiments, the eyewear frame 410 is configured to support the first and second lenses 418, 420 about the full perimeter of the first and second lenses 418, 420. In other embodiments, the eyewear frame 410 may be configured to support the first and second lenses 418, 420 about only a portion of each respective lens. In various embodiments, the eyewear frame 410 is configured to support a number of lenses other than two lenses (e.g., a single lens, a plurality of lenses, etc.). In particular embodiments, the lenses 418, 420 may include prescription lenses, sunglass lenses, or any other suitable type of lens (e.g., reading lenses, non-prescription lenses), which may be formed from glass or a suitable polymer.

In various embodiments, the eyewear frame 410 includes a first and second nose pad 422, 424, which may be configured to maintain the eyewear 400 adjacent the front of a wearer's face such that the lenses 418, 420 are positioned substantially in front of the wearer's eyes while the wearer is wearing the eyewear 400. In particular embodiments, the nose pads 422, 424 may comprise a material that is configured to be comfortable when worn by the wearer (e.g., rubber, plastic, etc.). In other embodiments, the nose pads 422, 424 may include any other suitable material (e.g., metal, etc.). In still other embodiments, the nose pads 422, 424 may be integrally formed with the frame 410.

The eyewear frame 410 includes a first and second hinge 426, 428 that attach the first and second temples 412, 414 to the frame first and second ends 402, 404, respectively. In various embodiments, the hinges 426, 428 may be formed by any suitable connection (e.g., tongue and groove, ball and socket, spring hinge, etc.). In particular embodiments, the first hinge 426 may be welded to, or integrally formed with, the frame 410 and the first temple 412, and the second hinge 428 may be welded to, or integrally formed with, the frame 410 and the second temple 414.

First and Second Temples

As shown in FIG. 4, the first temple 412, according to various embodiments, is rotatably connected to the frame 410 at a right angle to extend the first temple 412 substantially perpendicular, substantially parallel, or anywhere in between the right angle to the frame 410. The first temple 412 has a first and second end 412a, 412b. Proximate the first temple second end 412b, the first temple 412 includes an earpiece 413 configured to be supported by a wearer's ear. Similarly, the second temple 414, according to various embodiments, is rotatably connected to the frame 410 at a right angle to extend the second temple 414 substantially perpendicular, substantially parallel, or anywhere in between the right angle to the frame 410. The second temple 414 has a first and second end 414a, 414b. Proximate the second temple second end 414b, the second temple 414 includes an earpiece 415 configured to be supported by a wearer's ear.

Sensors

In various embodiments, one or more sensors 430 may be coupled to the frame 410, the first and second temples 412, 414, the first and second lenses 418, 420, or any other portion of the eyewear 400 in any suitable way. For instance, the one or more sensors 430 may be embedded into the eyewear 400, substantially permanently coupled to the eyewear 400 (e.g. using suitable welding or bonding techniques), and/or detachably coupled to the eyewear 400 (e.g. using a suitable spring-loaded clamp, etc.). In various embodiments, the one or more sensors 430 may be positioned at any point along the eyewear 400. For instance, an air pollution sensor may be disposed adjacent the first temple of the eyewear 400. The one or more sensors 430 may be formed on the inner (back) surface of the frame 410, the first and second temples 412, 414, the first and second lenses 418, 420, or any other portion of the eyewear 400. Also, in some embodiments, the one or more sensors 430 may be formed on the outer (front) surface of the frame 410, the first and second temples 412, 414, the first and second lenses 418, 420, or any other portion of the eyewear 400.

In various embodiments, the one or more sensors 430 that are coupled to the eyewear (or other wearable device) may include one or more environmental pollution sensors that are adapted to determine an individual's exposure to one or more environmental pollutants, and/or one or more health sensors to monitor the wearer's reaction to these pollutants. In various embodiments, the one or more environmental pollution sensors coupled to the eyewear or other environmental pollution monitoring device may include, for example, one or more of the following: (1) one or more ultraviolet light measurement devices (e.g. one or more devices that measure current levels of ultraviolet radiation); (2) one or more light pollutant samplers (e.g., one or more devices that measure current levels of ultraviolet light and blue light); (3) one or more noise pollutant samplers; (4) one or more radioactivity monitors; (5) one or more thermal pollutant samplers; (6) and/or one or more air sampling devices.

In various embodiments, the one or more health sensors may include, for example, one or more heart rate monitors, one or more electrocardiograms (EKGs), one or more electroencephalograms (EEGs), one or more thermometers, one or more transdermal transmitter sensors, one or more blood pressure sensors, one or more pulse oximeters, one or more respiration rate monitors, one or more front-facing cameras, one or more eye-facing cameras, one or more microphones, or any other suitable one or more sensors.

In particular embodiments, the one or more sensors 430 may be detachably or permanently coupled to the eyewear 400 in any suitable way. For example, in various embodiments, the sensors 430 may be embedded into the eyewear 400. In some embodiments, the sensors 430 may be positioned along the brow bar of the eyewear, the one or more of the temples 412, 414 of the eyewear, the lenses of the eyewear 418, 420.

Exemplary System Platform

As noted above, a system, according to various embodiments, is adapted to assess one or more levels of environmental pollution affecting a wearer of a wearable device. Various aspects of the system's functionality may be executed by certain system modules, including the Environmental Pollution Monitoring Module 300. The Environmental Pollution Monitoring Module 300 is discussed in greater detail below.

Environmental Pollution Monitoring Module

Figure 3:
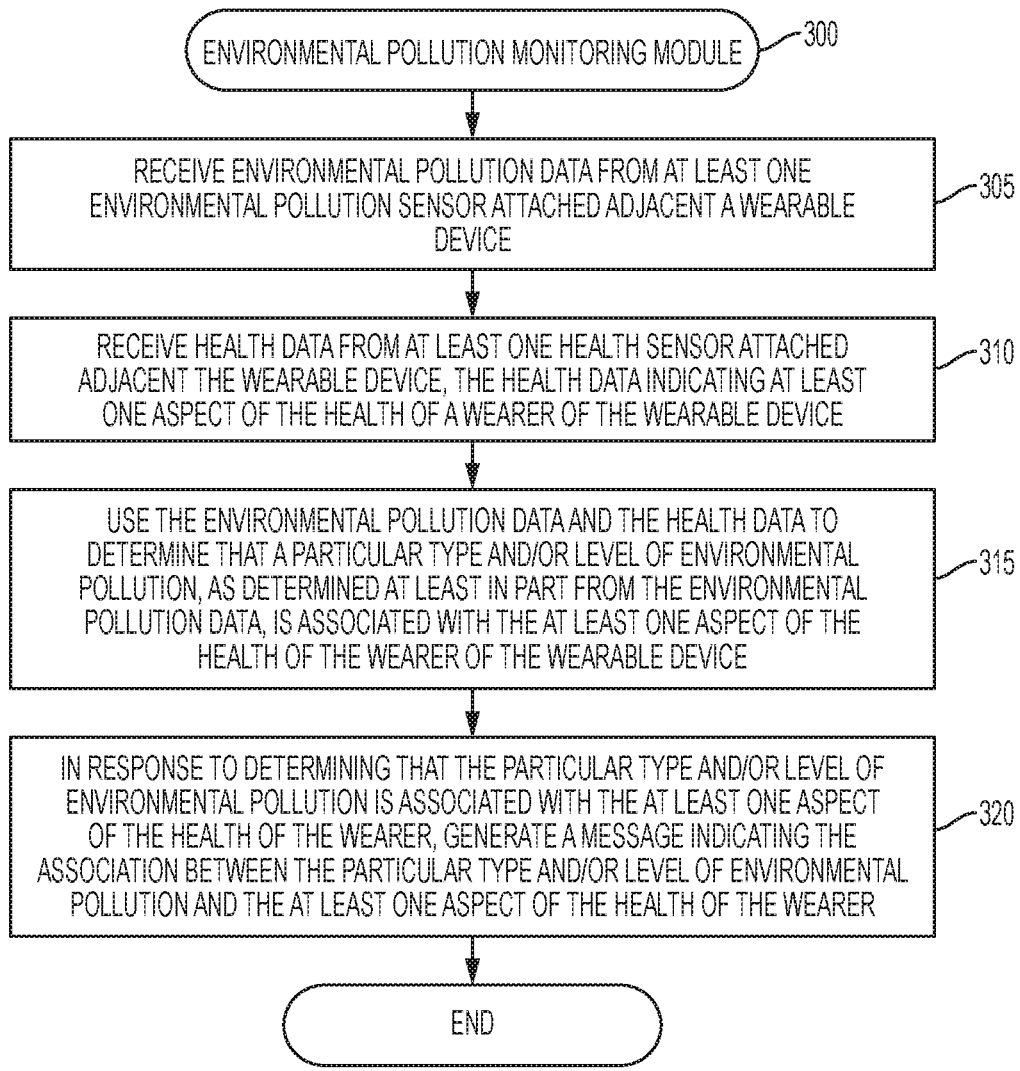
FIG. 3 depicts a flowchart that generally illustrates various steps executed by an Environmental Pollution Monitoring Module according to a particular embodiment.

FIG. 3 is a flow chart of operations performed by an exemplary Environmental Pollution Monitoring Module 300, which may, for example, run on the Environmental Pollution Monitoring Server 120, or any other suitable computing device (such as the one or more Environmental Pollution Monitoring Devices 400).

In various embodiments, the system begins, at Step 305 by receiving environmental pollution data from at least one environmental pollution sensor attached adjacent a wearable device. In particular embodiments, the at least one environmental pollution sensor attached to the wearable device (or other environmental pollution monitoring device) may include, for example, one or more of the following: (1) one or more ultraviolet light measurement devices (e.g. one or more devices that measure current levels of ultraviolet radiation); (2) one or more light pollutant samplers (e.g., one or more devices that measure current levels of ultraviolet light and blue light); (3) one or more noise pollutant samplers; (4) one or more radioactivity monitors; (5) one or more thermal pollutant samplers; (6) and/or one or more air sampling devices. In some embodiments, the environmental pollution data may relate to at least one characteristic associated with one or more of the following pollutants: (1) air pollutants (e.g., carbon monoxide, sulfur dioxide, nitrogen oxides, ozone, particulate matter, methane, non-methane hydrocarbons, etc.); (2) light pollutants (e.g., concentration of UV light exposure over time, light trespass, over-illumination, glare, light clutter, skyglow, exposure to blue light, etc.); (3) noise pollutants; (4) radioactive pollutants (e.g., alpha particle emissions, beta particle emissions, gamma ray emissions, etc.); (5) thermal pollutants; and/or (6) any other relevant pollutant.

In particular embodiments, the system may receive the environmental pollution data substantially automatically and/or on a substantially periodic basis (e.g., by the second, by the minute, hourly, daily, etc.). In other embodiments, the system may receive the environmental pollution data at least partially in response to receiving an indication from the wearer that the system should receive the environmental pollution data. For instance, the wearer may speak a voice command to the wearable device requesting that the device take an environmental pollution reading. In various other embodiments, the system may receive the environmental pollution data substantially continuously over a period of time (e.g., throughout the day, during daylight hours, etc.). In yet other embodiments, the system may modify how frequently the system receives the environmental pollution data based at least partially one or more conditions. For example the system may receive information periodically in response to determining that certain environmental conditions are present above a certain level (e.g., UV levels are above a certain threshold). When the system receives information that the UV level exceeds the threshold, the system may monitor the UV level substantially continuously.

In particular embodiments, the system may analyze the received environmental pollution data to determine at least one environmental pollution characteristic associated with the wearer's immediate environment. In various embodiments, the system may analyze the environmental pollution data by comparing various received environmental pollution data to predefined threshold levels. For example, the system may analyze the received environmental pollution data to determine whether there is a concentration of carbon monoxide above a predefined threshold level, a decibel level above a predefined threshold level, a smog level above a predefined threshold level, a blue light level above a predefined threshold level, or UV exposure (e.g., over a particular period of time) above a predefined threshold. In various embodiments, the system may analyze the received environmental pollution data based on an empirical measurement, such as the concentration of particles per million particles of the atmosphere. In various other embodiments, the system may analyze the received environmental pollution data based on a scaled rating. For example, where the system is determining the environmental pollution level of air pollution, the system may determine that the air pollution level is low, moderate, or high.

In various embodiments, the system may chart the analysis of the received environmental pollution data in a visual diagram. For example, the system may chart the changes in the air pollution level in a diagram displayed, for example, on the lens of the eyewear or on a separate display screen associated with the wearer. In various other embodiments, the system may chart the analysis of the received environmental pollution data substantially continuously.

In various embodiments, the system may analyze a particular received environmental pollution data at a particular time of day (e.g., morning, noon, night, etc.) and/or when the wearer arrives at a particular location (e.g., outdoors, in the city center, etc.). In various other embodiments, the system may analyze the environmental pollution data automatically or in response to receiving manual requests from the wearer. For example, the system may receive a voice command from the wearer requesting that the system determine the environmental pollution level around the wearer at that time.

At Step 310, the system is configured to receive health data from at least one health sensor attached adjacent the wearable device, the health data indicating at least one aspect of health of a wearer of the wearable device. In various embodiments, the health data may relate to at least one health characteristic associated with the wearer, and may include, for example: (1) the wearer's heart rate; (2) the wearer's heart rhythm; (3) the wearer's body temperature; (5) one or more images of the wearer or the wearer's immediate environment; (6) one or more sounds generated by the wearer's body (e.g., pulse) or the wearer's immediate environment; (7) the wearer's blood pressure; (8) the wearer's oxygen saturation level; (10) the wearer's pupil size; (11) the wearer's respiration rate; (12) one or more characteristics of the wearer's skin (e.g., paleness or redness); and/or (13) any other suitable attribute of the wearer or the wearer's environment.

In some embodiments, the system may receive the health data, for example, as an image or plurality of images captured by the eyewear. In particular embodiments, the system may receive such an image from an eye-facing camera associated with the wearable device. In some embodiments, the image captured by the wearable device may be an infrared image. In other embodiments, the system may receive the health data from the Environmental Pollution Database 140 to obtain a wearer's known sensitivities and/or medical conditions (e.g., asthma or known allergies).

In various embodiments, the system may capture the above-referenced health data substantially automatically and/or on a substantially periodic basis (e.g., by the second, by the minute, hourly, daily, etc.). In other embodiments, the system may receive the health data at least partially in response to receiving an indication from the wearer that the system should receive the health data. For instance, the wearer may speak a voice command to the wearable device requesting that the device take a heart rate reading. In various other embodiments, the system may receive the health data substantially continuously over a period of time (e.g., throughout the day, during daylight hours, etc.). In various embodiments, the system may store the health data in local or remote memory.

In particular embodiments, the system may receive a request from the wearer to have the health data received from the at least one health sensor at least partially in response to receiving environmental pollution data from the at least one environmental pollution sensor. For example, when the system receives environmental pollution data that indicates an environmental pollution sensor detects a certain air pollutant, the system may, at least partially in response to receiving the air pollution data, obtain a reading of the user's respiration rate. As a further example, the system may receive environmental pollution data from a UV sensor that indicates an environmental pollution sensor detects a certain level of UV light above a pre-determined threshold. At least partially in response to the UV light being above a pre-determined threshold, the system may receive health data from an eye-facing camera associated with the wearable device to help detect relevant changes in the wearer's skin (e.g., rashes or sunburn).

At Step 315, the system uses the environmental pollution data and the health data to determine that a particular type and/or level of environmental pollution, as determined at least in part from the environmental pollution data, is associated with the at least one aspect of the wearer's health of the wearable device. In particular embodiments, the system may use the environmental pollution data and the health data to determine that a particular type and/or level of environmental pollution is associated with at least one physical manifestation of an adverse reaction to an environmental pollutant (e.g., a respiratory rate, a heart rate, a skin condition, eye strain, disrupted circadian rhythm, or a brain-wave activity), at least one geographical location (e.g., GPS coordinates), and/or at least one time of day. In some embodiments, the system may determine that a particular type and/or level of environmental pollution is associated with both a geographic location and a specific time, with both a physical manifestation and a pollution rating, or any other combination of factors described herein.

In various embodiments, the system may determine that a particular type and/or level of environmental pollution, as determined at least in part from the environmental pollution data, is associated with at least one pollution characteristic. For example, an increase in respiratory rate may show a correlation with an increase in the level of sulfur dioxides. It should be understood from this disclosure that the system may determine that the environmental pollution associated with the aspect of the wearer's health is a combination of characteristics that allow the system to determine the effect of the multiple types and/or levels of environmental pollution on the wearer.

In various embodiments, the system stores, in memory, the determination that a particular type and/or level of environmental pollution is associated with the at least one aspect of the health of the wearer. In various embodiments, the system may store the association between the environmental pollution level and the aspect of the wearer's health substantially automatically and/or after (e.g., in response to) determining that a particular type and/or level of environmental pollution is associated with the at least one aspect of the wearer's health. In other embodiments, the system may store the association between the environmental pollution level and the aspect of the wearer's health after (e.g., at least partially in response to) receiving manual input from the wearer. In various embodiments, the system may store the association between the environmental pollution level and the aspect of the wearer's health in a suitable Database 140.

At Step 320, in response to determining that the particular type and/or level of environmental pollution is associated with the at least one aspect of the wearer's health, the system generates a message indicating the association between the particular type and/or level of environmental pollution and the at least one aspect of the wearer's health. In various embodiments, the system may generate a message to the wearer or other suitable individual of the association between the particular type and/or level of environmental pollution and the at least one aspect of the health of the wearer. For example, in some embodiments, the system may notify the wearer and/or the wearer's physician of the association of a particular environmental pollution to a particular aspect of the wearer's health (e.g., the system may notify the wearer that they appear to have an allergy to ragweed). In various embodiments, the system pools data from multiple wearers within a geographic area and may inform health officials regarding geographically larger environmental pollution trends.

In particular embodiments, the system may generate a message to the wearer of the association between the particular type and/or level of environmental pollution and the at least one aspect of the wearer's health, for example, by displaying an image on the lens of the eyewear 400, or a display screen associated with the eyewear 400, or by communicating the association through an audio speaker to the wearer. In some embodiments, the system may generate a message to the wearer of the association by sending a notification to the wearer's mobile device. In particular embodiments, the system may generate a message via an electronic communication such as email or SMS. In certain embodiments, the system may generate a message of all associations made over a period of time (e.g., a day, week, month, etc.).

In other embodiments, the system may generate a message of a particular association between the particular type and/or level of environmental pollution and the at least one aspect of the health of the wearer after (e.g., at least partially in response to) detecting a particular event. For example, the system may generate a message of the association in response to the system ceasing to detect the physical manifestation of an adverse reaction to an environmental pollutant and/or at least partially in response to the system detecting a decrease below a predetermined threshold level of an environmental pollutant. In other embodiments, the system may generate a message of the association based on historical data or the data of other users. For example, the system may have made an association between particular environmental pollution data (e.g., high smog levels) and particular health data (e.g., increased wearer heart rate) at a given time or geographical location in the past, and may alert the wearer when the wearer approaches a given geographical location where the environmental pollution at issue has been reported above a threshold level by other wearers. In still other embodiments, the system may generate a message at a certain time of day or at a certain geographical location. As an example, the system may generate a message to the wearer of an association between the environmental pollution and an aspect of the wearer's health at the end of the day or when the user is approaching, or en route to, a certain geographical location that is associated with environmental pollution factors that the system has determined may adversely impact the wearer's health.

In various embodiments, the system may provide the wearer with one or more suggested actions to address or ameliorate the effects of environmental pollution (e.g., that the system has determined adversely impacts the wearer's health). In various embodiments, the system may provide one or more suggested actions to the wearer in any suitable way. For example, the system may provide one or more suggested actions to the wearer by displaying an image on the lens of the eyewear, or on a display screen associated with the wearer, or through an audio speaker. In some embodiments, the system provides one or more suggested actions to the wearer by sending a notification to the wearer's mobile by email, or by SMS.

In various embodiments, the one or more suggested actions to address the environmental pollution may include one or more preventative health measures. In particular embodiments, the one or more suggested actions may include, for example: (1) wearing an anti-pollution mask; (2) applying sunscreen to the wearer's skin; (3) utilizing ear protection; (4) wearing protective lenses; (5) abstaining from vigorous physical activity during a certain time period; (6) taking an alternate route to a destination; and/or (7) utilizing a suitable medication to address the environmental pollution. In other embodiments, the one or more suggested actions to address the environmental pollution level may include suggesting that the wearer visit one or more websites containing information on preventative health measures or environmental pollution. As another example, where the environmental pollution is at an elevated state, the system may suggest a nearby location where preventative health products may be purchased to aid in ameliorating adverse effects of environmental pollution.

In various embodiments, the system may provide one or more suggested actions to the wearer to address or ameliorate the effects of environmental pollution immediately after the system notifies the wearer of the association between the wearer's physical condition and the environmental pollution level. In other embodiments, the system may provide one or more suggested actions to the wearer after (e.g., in response to) detecting a particular environmental condition. For example, the system may provide one or more suggested actions to the wearer after the system detects a change in the level of a particular environmental pollutant. In some embodiments, the system may provide one or more suggested actions to the wearer within a particular period of time after the system notifies the wearer of the association between the wearer's physical condition and the environmental pollution level. For instance, the system may provide one or more suggested actions to the wearer one hour after the system associates a physical condition of the wearer (e.g. wheezing) with an environmental pollutant (e.g. cigarette smoke). In still other embodiments, the system may provide one or more suggested actions to the wearer at a particular time of day or when the wearer reaches a particular geographical area.

In various embodiments, the system, when executing the Environmental Pollution Monitoring Module 300, may omit particular steps, perform particular steps in an order other than the order presented above, or perform additional steps not discussed directly above. It should also be understood that various steps executed "in response to" a particular event occurring, or a particular condition being satisfied, may also be executed "at least partially in response to" the particular event occurring or the particular condition being satisfied.

Exemplary User Experience

Individual Tracking

In a particular example of using the Environmental Pollution Monitoring Module 300 to monitor environmental pollution, the wearer may put on the one or more Environmental Pollution Monitoring Devices 400 in the morning and continue to wear the device throughout the day. During this time, the system may, for example, track air pollution, including sulfur dioxide, nitrogen oxides, ozone, particulate matter, carbon monoxide, hydrocarbons, and/or volatile organic compounds using an air pollution sensor associated with the one or more Environmental Pollution Monitoring Devices 400. The system may then use a GPS device associated with the one or more Environmental Pollution Monitoring Devices 400 or other device associated with the wearer (e.g., the user's smartphone) to track the location of the wearer contemporaneously with the concentration of soot particulates and sulfur dioxide levels measured by the air pollution sensor and/or any other types of environmental pollution discussed herein and/or detectable by an environmental pollution sensor. The system may use this information to determine the relative localized level of environmental pollution around the wearer.

The system may store the environmental pollution levels as historical environmental pollution data and chart the highs and lows of various pollutants over the course of a week or other predetermined time period, to determine the times and days when the user experiences the highest and lowest pollution levels. For example, in geographical locations where the environmental pollution levels are relatively high from 6:00 a.m. to 9:00 a.m. and from 4:00 p.m. to 7:00 p.m., the system may notify the wearer that the highest pollution levels relative to the wearer's geographic locations during those times occurs from 6:00 a.m. to 9:00 a.m. and from 4:00 p.m. to 7:00 p.m. The wearer may then use this information to alter the wearer's activities so that the wearer can avoid the highest peaks of environmental pollution.

Moreover, the one or more Environmental Pollution Monitoring Devices 400 may detect and track the wearer's current health data indicating at least one aspect of health of the wearer while monitoring the environmental pollution levels. In this manner, the Environmental Pollution Monitoring Module 300 can detect any change in the at least one aspect of health of the wearer and make any correlation between the health change and any detected environmental pollution.

Predictive Modeling

Just as the system may track environmental pollution relative to the wearer over a period of time, the system, in a particular example, may also predictively model environmental pollution levels based on historical data other than time. The system may generate this model, for example, by tracking the environmental pollution levels relative to the wearer, in combination with some other data, for example, weather data, traffic data, event data, meteorological data, etc. The system may then generate a predictive model that will enable the wearer to take proactive, rather than reactive measures to ameliorate the effects of environmental pollution. For instance, the system may use historic data regarding the time and locations of travel with live traffic data to generate an estimation of environmental pollution over a given route when certain weather events occur.

According to various embodiments, the Environmental Pollution Monitoring System 100 may utilize travel information from one or more travel sources associated with a smartphone, computer, website, network, or other computing device or system utilized by the wearer. For example, the wearer may have travel information stored in a calendar, email, website, or database. The Environmental Pollution Monitoring System 100 may detect a pending travel location and date range, and in response, utilize historical or stored environmental pollution data associated with that location to determine any potential for health problems at that time and location for the wearer. The potential for health problems may be based on the level of environmental pollution, the type of environmental pollution, and/or the wearer's historical or predicted reaction to the type and/or level of predicted environmental pollution during travel. The wearer may use this information to plan their travels accordingly.

Regional Modeling

In a further particular example of the Environmental Pollution Monitoring Module 300 of the One or More Wearable Environmental Pollution Monitoring Devices 400 monitoring environmental pollution levels, the system may track multiple wearers within a geographical location to provide an accurate measure of the environmental pollution over a larger area. The system may track multiple wearers by storing the environmental pollution data for multiple wearers and analyzing the data to calculate the environmental pollution level over the area the data covers.

For example, if multiple wearers encounter a particular environmental pollution in a particular area that is distinct from the environmental pollution a particular wearer normally encounters, the system may provide the particular wearer with a notification that the environmental pollution in the particular area is different from the environmental pollution the wearer normally encounters. For instance, if a particular wearer travels a different route or travels to a different location from their normal routine, the system may alert the wearer of particular environmental pollutants prior to the wearer arriving in that particular location. The system may also advise the wearer to take alternate routes in order to avoid the different environmental pollution that the wearer does not normally encounter.

Health Monitoring

In a further particular example of using the Environmental Pollution Monitoring Module 300 of the One or More Wearable Environmental Pollution Monitoring Devices 400 to monitor environmental pollution levels, the system tracks the wearer's response to various environmental pollutants throughout the day via the wearable device. The system tracks the wearer's reaction to various environmental pollutants by monitoring the wearer's pupil size, heart rate, respiration rate, skin condition (e.g., skin color, hives, rashes), etc. The system may also monitor changes in the wearer's pupil size, heart rate, perspiration level, respiration rate, skin condition, or other health data using an eye-facing camera.

For example, if the wearer has an abnormal increase in their respiratory rate simultaneously with an abnormal environmental pollution level, the system may alert the wearer or other individual (e.g., the wearer's physician) to the predicted sensitivity. The system may then provide instructions to the wearer suggesting the wearer take measures to ameliorate their condition and suggest other ways to avoid exposure to the pollutant in the future. The system may, for example, provide these suggestions to the wearer through a suitable notification sent to the wearer's mobile device.

CONCLUSION

Many modifications and other embodiments of the invention will come to mind to one skilled in the art to which this invention pertains, having the benefit of the teaching presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A non-transitory computer-readable medium storing computer-executable instructions for:
receiving an indication from a wearer of a wearable device, the indication being used for indicating to receive environmental pollution data, the wearable device comprising a pair of eyewear;

receiving present environmental pollution data measured from at least one environmental pollution sensor attached adjacent the wearable device in response to receiving the indication;

obtaining stored historical environmental pollution data being measured by the at least one environmental pollution sensor attached adjacent the wearable device historically;

receiving a request from the wearer of the wearable device, the request being used for indicating to receive health data;

receiving the health data from at least one health sensor attached adjacent the wearable device in response to receiving the present environmental pollution data and in response to receiving the request, the health data indicating at least one aspect of health of the wearer's health, the at least one aspect of the wearer's health comprising a respiratory ailment;

receiving a voice command from the wearer, the voice command being used for indicating to determine a present type or level of environmental pollution;

determining the present type or level of environmental pollution around the wearer at least partially based on the present environmental pollution data in response to receiving the voice command;

determining that the present type or level of environmental pollution is associated with the at least one aspect of the wearer's health by using the present environmental pollution data, the historical environmental pollution data, and the health data;

in response to determining that the present type or level of environmental pollution is associated with the at least one aspect of the wearer's health, generating a message comprising an association between the present type or level of environmental pollution and the at least one aspect of the wearer's health, the message indicating that the wearer is having an adverse reaction to the present type or level of environmental pollution; and presenting, on at least one lens of the pair of eyewear, the message comprising the association and a chart illustrating changes in environmental pollution in a diagram.

2. The non-transitory computer-readable medium of claim 1, wherein the at least one health sensor is embedded within the pair of eyewear.

3. The non-transitory computer-readable medium of claim 2, wherein the at least one health sensor comprises a camera that is positioned to capture an image of at least a portion of the wearer's body when the wearer is wearing the wearable device.

4. The non-transitory computer-readable medium of claim 3, wherein:
the at least one environmental pollution sensor comprises a UV sensor; and
the at least one aspect of the wearer's health further comprises a presence of a sunburn on the wearer's skin.

5. The non-transitory computer-readable medium of claim 4, wherein:
the present and historical environmental pollution data comprises UV data received from the UV sensor; and
the computer-readable medium further stores computer-executable instructions for:
determining, based at least in part on the UV data and the image, an amount of UV exposure the wearer's skin can tolerate before becoming sunburned.

6. The non-transitory computer-readable medium of claim 3, wherein:

the at least one environmental pollution sensor comprises a sensor for sensing a presence of at least one airborne allergen.

7. The non-transitory computer-readable medium of claim 6, wherein:
the at least one airborne allergen comprises smog; and
the at least one aspect of the wearer's health comprises asthma.

8. The non-transitory computer-readable medium of claim 6, wherein the at least one airborne allergen comprises smog.

9. The non-transitory computer-readable medium of claim 2, wherein the at least one health sensor comprises an oxygen saturation monitor.

10. The non-transitory computer-readable medium of claim 1, further storing computer-executable instructions for:
receiving travel information associated with the wearer from one or more travel sources;
determining from the travel information a travel location and a date range associated with the travel location;
in response to determining from the travel information the travel location and the date range, utilize historical or stored environmental pollution data associated with the travel location to determine a potential for a health problem at the travel location during the date range; and
notifying the wearer of the potential for the health problem at the travel location during the date range.

11. A computer-implemented method of monitoring environmental pollution adjacent a pair of eyewear, the method comprising:
receiving, by at least one processor, an indication from a wearer of a wearable device, the indication being used for indicating to receive environmental pollution data, the wearable device comprising the pair of eyewear;
receiving, by the at least one processor, present environmental pollution data measured from at least one environmental pollution sensor attached adjacent the wearable device in response to receiving the indication;
obtaining, by the at least one processor, stored historical environmental pollution data being measured by the at least one environmental pollution sensor attached adjacent the wearable device historically;
receiving, by the at least one processor, a request from the wearer of the wearable device, the request being used for indicating to receive health data;
receiving, by the at least one processor, the health data from at least one health sensor attached adjacent the wearable device in response to receiving the present environmental pollution data and in response to receiving the request, the health data indicating at least one aspect of health of the wearer's health, the at least one aspect of the wearer's health comprising a respiratory ailment;
receiving, by the at least one processor, a voice command from the wearer, the voice command being used for indicating to determine a present type or level of environmental pollution;
determining, by the at least one processor, the present type or level of environmental pollution around the wearer at least partially based on the present environmental pollution data in response to receiving the voice command;
determining, by the at least one processor, that the present type or level of environmental pollution is associated with the at least one aspect of the wearer's health by using the present environmental pollution data, the historical environmental pollution data, and the health data;

in response to determining that the present type or level of environmental pollution is associated with the at least one aspect of the wearer's health, generating, by the at least one processor, a message comprising an association between the present type or level of environmental pollution and the at least one aspect of the wearer's health, the message indicating that the wearer is having an adverse reaction to the present type or level of environmental pollution; and presenting, by the at least one processor on at least one lens of the pair of eyewear, the message comprising the association and a chart illustrating changes in environmental pollution in a diagram.

12. The computer-implemented method of claim 11, further comprising:

receiving travel information associated with the wearer from one or more travel sources;

determining from the travel information a travel location and a date range associated with the travel location;

in response to determining from the travel information the travel location and the date range, utilize historical or stored environmental pollution data associated with the travel location to determine a potential for a health problem at the travel location during the date range; and notifying the wearer of the potential for the health problem at the travel location during the date range.

13. The computer-implemented method of claim 11, wherein:

the at least one environmental pollution sensor comprises a UV sensor; and the at least one aspect of the wearer's health further comprises a presence of a sunburn on the wearer's skin.

14. The computer-implemented method of claim 13, wherein the at least one health sensor comprises a camera that is positioned to capture an image of at least a portion of the wearer's body when the wearer is wearing the wearable device.

15. The computer-implemented method of claim 14, wherein the present and historical environmental pollution data comprises UV data received from the UV sensor; and wherein the method further comprises:

determining, based at least in part on the UV data and the image, an amount of UV exposure the wearer's skin can tolerate before becoming sunburned.

16. The computer-implemented method of claim 11, wherein:

the at least one environmental pollution sensor comprises a sensor for sensing a presence of at least one airborne allergen.

17. The computer-implemented method of claim 16, wherein:

the at least one airborne allergen comprises smog; and the at least one aspect of the wearer's health comprises asthma.

18. The computer-implemented method of claim 11, wherein the at least one health sensor comprises an oxygen saturation monitor.

* * * * *